US011065252B2

(12) United States Patent
Adam et al.

(10) Patent No.: US 11,065,252 B2
(45) Date of Patent: Jul. 20, 2021

(54) TREATMENT OF ROSACEA WITH P38 AND ERK KINASE PATHWAY INHIBITORS

(71) Applicant: Albany Medical College, Albany, NY (US)

(72) Inventors: Alejandro P. Adam, Hudson, NY (US); Edward Wladis, Delmar, NY (US)

(73) Assignee: Albany Medical College, Albany, NY (US)

( * ) Notice: Subject to any disclaimer, the term of this patent is extended or adjusted under 35 U.S.C. 154(b) by 199 days.

(21) Appl. No.: 16/098,995

(22) PCT Filed: May 5, 2017

(86) PCT No.: PCT/US2017/031185
§ 371 (c)(1),
(2) Date: Nov. 5, 2018

(87) PCT Pub. No.: WO2017/192928
PCT Pub. Date: Nov. 9, 2017

(65) Prior Publication Data
US 2019/0142831 A1 May 16, 2019

Related U.S. Application Data

(60) Provisional application No. 62/332,690, filed on May 6, 2016.

(51) Int. Cl.
*A61K 31/519* (2006.01)
*A61P 27/02* (2006.01)
*A61P 37/02* (2006.01)
*A61P 29/00* (2006.01)

(52) U.S. Cl.
CPC ............ *A61K 31/519* (2013.01); *A61P 27/02* (2018.01); *A61P 29/00* (2018.01); *A61P 37/02* (2018.01)

(58) Field of Classification Search
None
See application file for complete search history.

(56) References Cited

U.S. PATENT DOCUMENTS

| 4,837,378 | A | 6/1989 | Borgman | |
|---|---|---|---|---|
| 8,350,026 | B2 * | 1/2013 | Felding | C07D 405/12 544/96 |
| 8,513,440 | B2 * | 8/2013 | Winssinger | A61P 11/06 549/270 |
| 9,220,788 | B2 | 12/2015 | Davis et al. | |
| 2005/0271661 | A1 * | 12/2005 | Manivasakam | A61K 38/13 424/144.1 |
| 2008/0027070 | A1 * | 1/2008 | Noronha | C07D 401/12 514/252.18 |
| 2015/0232883 | A1 | 8/2015 | Dahlman et al. | |

FOREIGN PATENT DOCUMENTS

| WO | 2007082780 A1 | 7/2007 | |
|---|---|---|---|
| WO | 2008020028 A1 | 2/2008 | |
| WO | 2009/101199 | 8/2009 | |
| WO | WO2013/000872 | * 1/2013 | ............... C12Q 1/68 |

OTHER PUBLICATIONS

Chung et al., "STAT3 Serine Phosphorylation by ERK-Dependent and -Independent Pathways Negatively Modulates Its Tyrosine Phosphorylation" Molecular and Cellular Biology vol. 17 No. 11 pp. 6508-6516 (Year: 1997).*
Mocsai et al., "Kinase Pathways in Chemoattractant-Induced Degranulation of Neutrophils: The Role of p38 Mitogen-Activated Protein Kinase Activated by Src Family Kinases" Journal of Immunology vol. 164 pp. 4321-4331 (Year: 2000).*
Mastrofranesco et al., "Azelaic acid modulates the inflammatory response in normal human keratinocytes through PPAR-gamma activation" Experimental Dermatology vol. 19 pp. 813-820 (Year: 2010).*
Vaubel et al., "Retarded low-dose doxycycline for EGFR or MEK inhibitor-induced papulopustular rash" JEADV vol. 28 pp. 1685-1689 (Year: 2014).*
Wladis et al. "Activation of p38 and Erk Mitogen-Activated Protein Kinases Signaling in Ocular Rosacea," Invest Ophthalmol Vis Sci, Feb. 1, 2017 (Feb. 1, 2017), vol. 58 No. 2, pp. 843-848, entire document.
International Search Report Form PCT/ISA/220, International Application No. PCT/US2017/031185, pp. 1-8, dated Jul. 26, 2017.
Extended European Search Report, PCT/US2017/031185, pp. 1-8, dated Sep. 5, 2019.

* cited by examiner

*Primary Examiner* — Eric Olson
(74) *Attorney, Agent, or Firm* — Bond Schoeneck and King PLLC; David Nocilly

(57) ABSTRACT

A treatment for ocular rosacea using p38 and Erk kinase pathway inhibitors, which are believed to block the initial reaction to rosacea triggers and thus make it possible to prevent or minimize the skin reaction. The treatment is premised on a careful analysis of the alteration of cell-signaling pathways that facilitate the development of rosacea, which led to the identification of discrete targets for highly specific therapeutic intervention in the management of rosacea.

6 Claims, 9 Drawing Sheets
Specification includes a Sequence Listing.

TREATMENT OF ROSACEA WITH P38 AND ERK KINASE PATHWAY INHIBITORS

CROSS-REFERENCE TO RELATED APPLICATIONS

The present application claims priority to U.S. Provisional Application No. 62/332,690, filed on May 6, 2016.

BACKGROUND OF THE INVENTION

1. Field of the Invention

The present invention relates to treatment for rosacea and, more particularly, to the use of certain intracellular signaling pathway inhibitors.

2. Description of the Related Art

Rosacea is a chronic condition that affects the facial and ocular skin. The causes of rosacea are not well understood and it has recently been suggested that a genetic predisposition may act in combination with environmental factors. As described by the National Rosacea Society Expert Committee on the Classification and Staging of Rosacea, rosacea encompasses multiple presentations, including ocular rosacea (OR), erythematotelangiectatic rosacea (ETR), papulopustular rosacea (PPR), phymatous rosacea (PHR).

The clinical manifestations are different among these four presentations of primary rosacea, which may result from different pathophysiological mechanisms. PPR and PHR are accompanied by inflammatory lesions, while OR and ETR are not. In fact, according to the Consensus Recommendations from the American Acne & Rosacea Society, ETR is the most common presentation, and is "clinically defined as diffuse centrofacial erythema secondary to sustained vasodilation without inflammatory lesions and often with symptoms of skin sensitivity (e.g., stinging, burning)." It becomes clear to one in the art that preventing inflammation may not be adequate to treat patients with ETR. In fact, topical skin steroids, a common anti-inflammatory treatment, can lead to rosacea-like symptoms.

The prevalent clinical manifestation of ETR is the intermittent facial flushing (called "flares") that can result in constant facial erythema (skin redness on the central region of the face). Ocular rosacea occurs in more than 50% of the individuals with other types of rosacea, but can occur also independently of facial rosacea. Patients with OR show distinct erythema on the eyelids and other regions of the skin surrounding the eyes, which can lead to dry eye disease, pain and corneal damage. Rosacea flares can be induced by different "triggers," depending on the patient. Common triggers include sun exposure, alcohol consumption, hot or cold weather, emotional stress and spicy food.

Multiple diseases can cause erythema (red face). Although this redness may be called "rosacea" in colloquial language, one in the art will recognize that primary rosacea (i.e., rosacea that is not due to another cause) is a different disease than rosacea-like features that may appear secondary to (i.e., caused by) other conditions, such as lupus erythematosus, sarcoidosis, scleroderma and others, and, while rosacea may be idiopathic in nature, a diagnosis of rosacea truly rests on tell-tale histopathologic and clinical features. For example, the lupus butterfly rash or malar rash associated with lupus erythematosus is often confused with rosacea, even leading to wrong diagnoses due to a similar skin appearance, despite drastically different mechanisms of action of these two diseases. Sarcoidosis can cause papules on the skin of the face as well as maculopapular rashes on other sites of the body. The facial papules can also be confused with rosacea, even though these are two very dissimilar diseases. Scleroderma is an autoimmune disease characterized by skin thickening and variable internal organ damage. Among other clinical features, patients commonly show small vessel vasculopathy, including capillary abnormalities and telangiectasias. The latter are a common feature of rosacea, but again do not share a similar disease mechanism, and the aforementioned diagnoses may lack the perifollicular infiltrates that are consider pathognomonic of rosacea.

Furthermore, Sweet's syndrome is an acute febrile neutrophilic dermatosis (skin inflammation) that is characterized by tender erythematous skin lesions. Redness in the skin is also a hallmark of ETR and other forms of rosacea. In fact, patients with facial Sweet's syndrome may mimic rosacea, leading to a misdiagnosis. However, the lack of fever and neutrophil infiltrate in rosacea patients clearly shows that these are two different diseases. Pityriasis rosea (sometimes erroneously called pityriasis rosacea) is a common skin affecting mainly adolescents and young adults aged 10-35 years old. It is self-limiting and resolves without treatment within three months. It is thus imperative to understand the differences between rosacea and other diseases that may share some common clinical features but a different underlying reason and different histopathologic features, as the treatment for one or the others are radically different in nature and patients truly suffer from different entities.

Several treatment options have been designed to address rosacea, and the multiplicity of therapies underscores the lack of efficacy of any particular one. Lifestyle modifications, eyelid hygiene, topical and oral medications, laser and light-based therapies, and surgical interventions have all been employed in the management of rosacea, although the results of these treatments have not been uniformly effective and this ailment remains incurable. In fact, current modalities either address inflammation in a very general sense (i.e., corticosteroids, dietary modifications, non-steroidal agents, antibiotics, etc.) or attempt to reverse existing damage distal to the site of the pathology (i.e., meibomian gland probing, corneal surgery to address perforations, etc.). Consequently, current therapeutic armamentaria fail to tackle the immunologic and cellular aberrancies of this disease, and thus cannot suppress rosacea in a highly targeted, specific fashion.

Recent studies have advanced our comprehension of the biologic aberrancies inherent to rosacea by assessing the concentrations of 48 individual cytokines, chemokines, and angiogenic factors in cutaneous biopsies of the disease and in control patients, and by identifying statistically-significant enrichments of interleukins-1β and -16, stem cell factor, monocyte chemoattractant protein-1, and the monokine induced by interferon gamma. Given that these molecules have been previously associated with the innate immune system, follow up studies were performed to better understand this process. It was previously demonstrated that there was an enrichment of toll-like receptors in cutaneous biopsies of ocular rosacea; these proteins provide constant surveillance against invading pathogens, and, upon stimulation, coordinate an innate immune response. Perhaps most excitingly, the number of toll-like receptors correlated with the presence of the vascular abnormalities CD105 and intercellular-adhesion molecule-1 in cutaneous preparations of ocular rosacea, further implicating this variant of immunity in the disease.

Despite the epidemiologically-rich nature of rosacea and its significant impact on the lives of patients that suffer from it, current treatment options are woefully inadequate. In fact, treatment options are generally non-specific and do not target the cellular and immunologic features that distinguish the disease from normal, healthy skin. As such, enhancements in our comprehension of the biology of rosacea would ideally facilitate the development of new highly specific interventions in a highly translational manner. Accordingly, there is a need in the art to further refine the understanding of the cellular biology of rosacea so that adequate treatments can be developed.

BRIEF SUMMARY OF THE INVENTION

The present invention is a method of treating rosacea comprising the step of administering a pharmaceutically effective amount of a p38 kinase pathway inhibitor, an Erk kinase pathway inhibitor, or a combination thereof. At least one of the p38 kinase pathway inhibitor or the Erk kinase pathway inhibitor may be a small molecule compound, a synthetic peptide, a nucleic acid, a gene delivery system, or a gene therapy vector that performs gene editing. The step of administering a pharmaceutically effective amount of a p38 kinase pathway inhibitor, the Erk kinase pathway inhibitor, or the combination thereof may comprise concurrently administering both the p38 kinase pathway inhibitor and the Erk kinase pathway inhibitor. The p38 kinase pathway inhibitor or the Erk kinase pathway inhibitor can inhibit an upstream activator such as Rac1, Rac2, Rac3, CDC42, a member of Ras family of proteins, a member of the Raf family of proteins, Mek1, Mek2, MKK3, MKK6, Ask1, Ask2, MEKK1, MEKK4 MLK1, MLK2, MLK3, Sos, Src, FAK, IRS1, IRS2 or IRS3. The p38 kinase pathway inhibitor or the Erk kinase pathway inhibitor can inhibit a downstream effector such as MSK1, MSK2, PRAK, p90RSK, Elk1, Creb, Myc, ATF2, ATF3, ATF4, MEF2, STAT1, STAT3, p53, MAPKAP2, HSP27, NFAT2, NFAT4, SRF, cPLA2, STMN1, Tau, Cdc25B, Max, GADD153 and Sap1. The p38 kinase pathway inhibitor, the Erk kinase pathway inhibitor, or the combination may be administered topically, orally, or by injection. An amount of an ultraviolet light blocker, a moisturizer, an antibiotic, a preservative, a fragrance, an artificial color, a flavor, and combinations thereof may also be used.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a graph of phosphoprotein profiler array data showing increased phosphorylation of (A) p38 and (B) Erk kinases in eyelid biopsies from patients with ocular rosacea compared to age-matched controls. *, $p<0.05$; #, $p<0.1$ (Two-tailed Student's T test, n=4 controls and 4 rosacea eyelids);

FIG. 2 is series of images of a Western blot analysis to confirm the initial results obtained with the protein profiler arrays where (A) is sample Western blot bands corresponding to the phosphorylated and total forms of each protein and (B) is band quantification and expressed as a normalized result (p-protein/total protein). *, $p<0.05$ (One-tailed Student's T test, n=10 controls and 14 rosacea eyelids);

Figure 5:
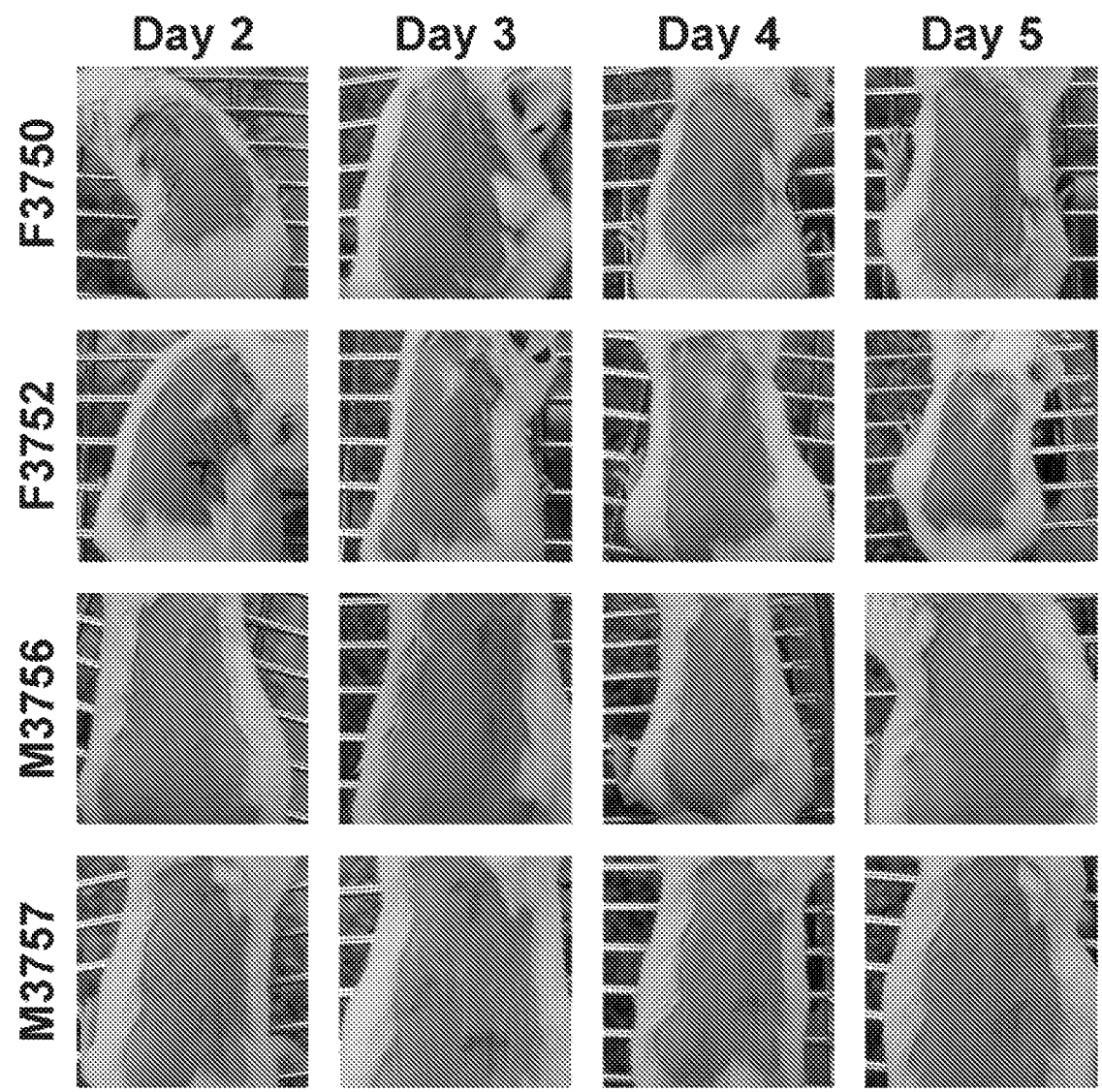
FIG. 5 is a series of images of the shaved backs of the mice of Example 2 showing the three treatment spots in each mouse for days 2, 3, 4 and 5 (Day 1 is the first treatment day) where no skin changes can be observed after the application of either a vehicle cream or a cream containing trametinib.
Figure 6:
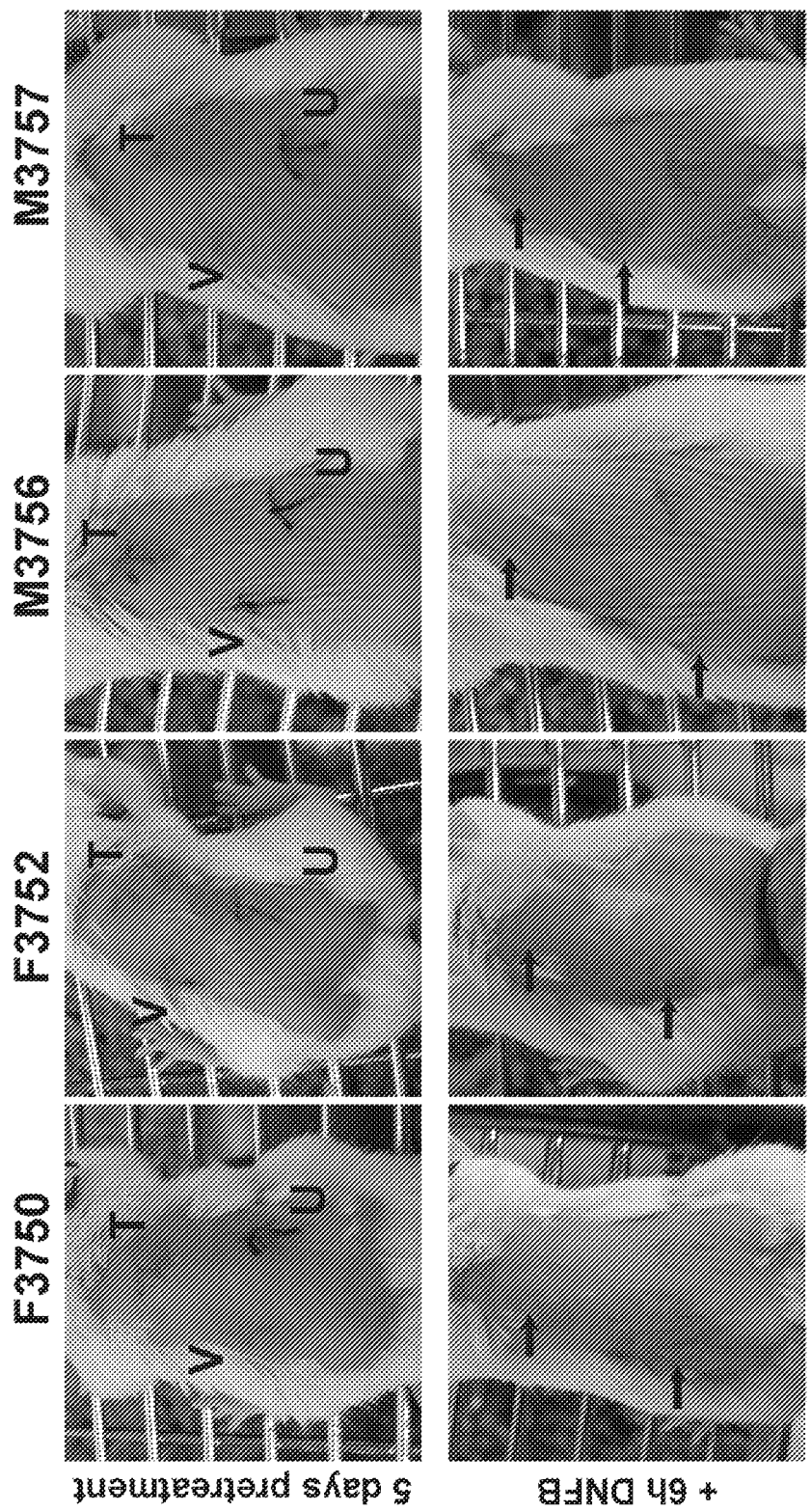
Figure 7:
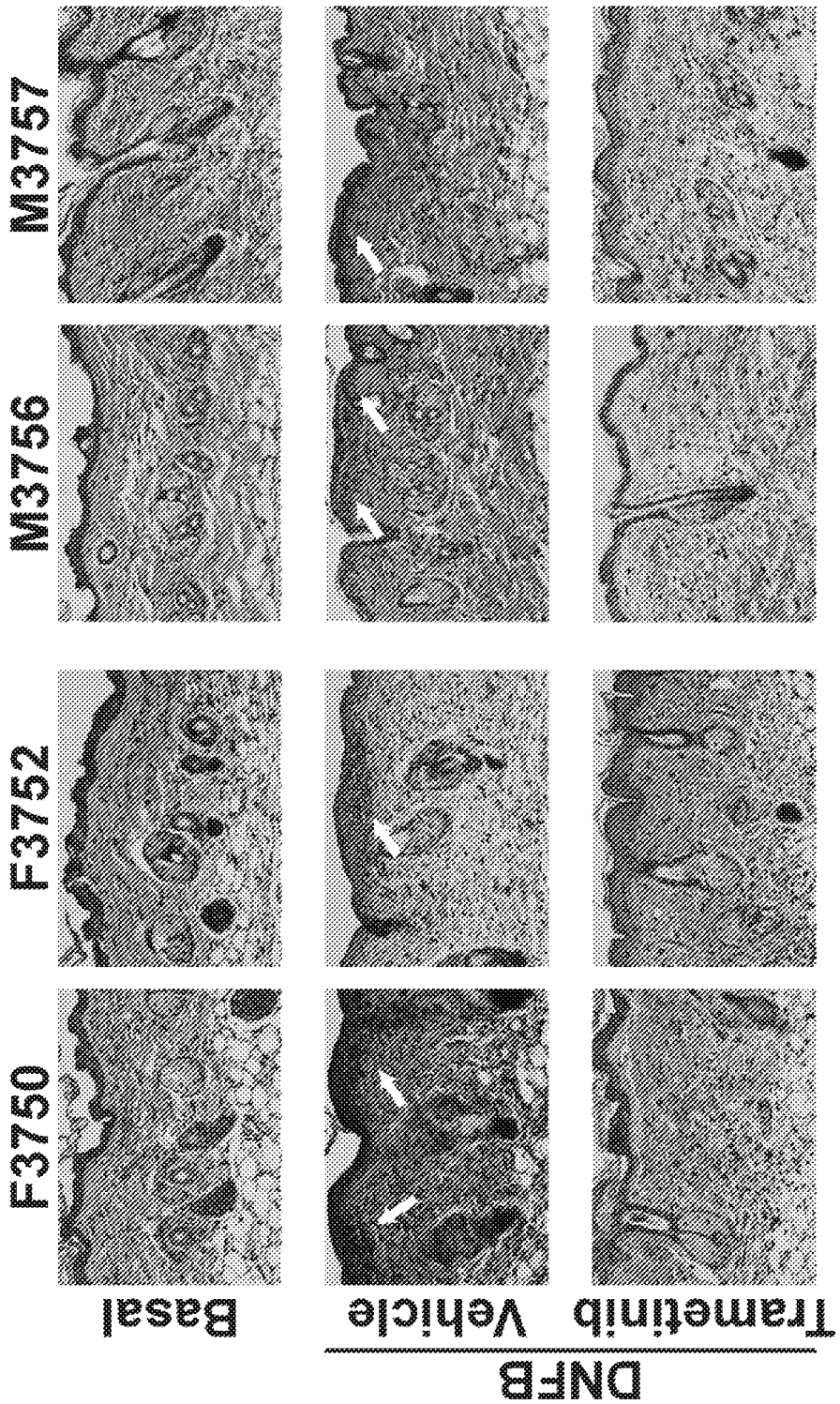
Figure 8:
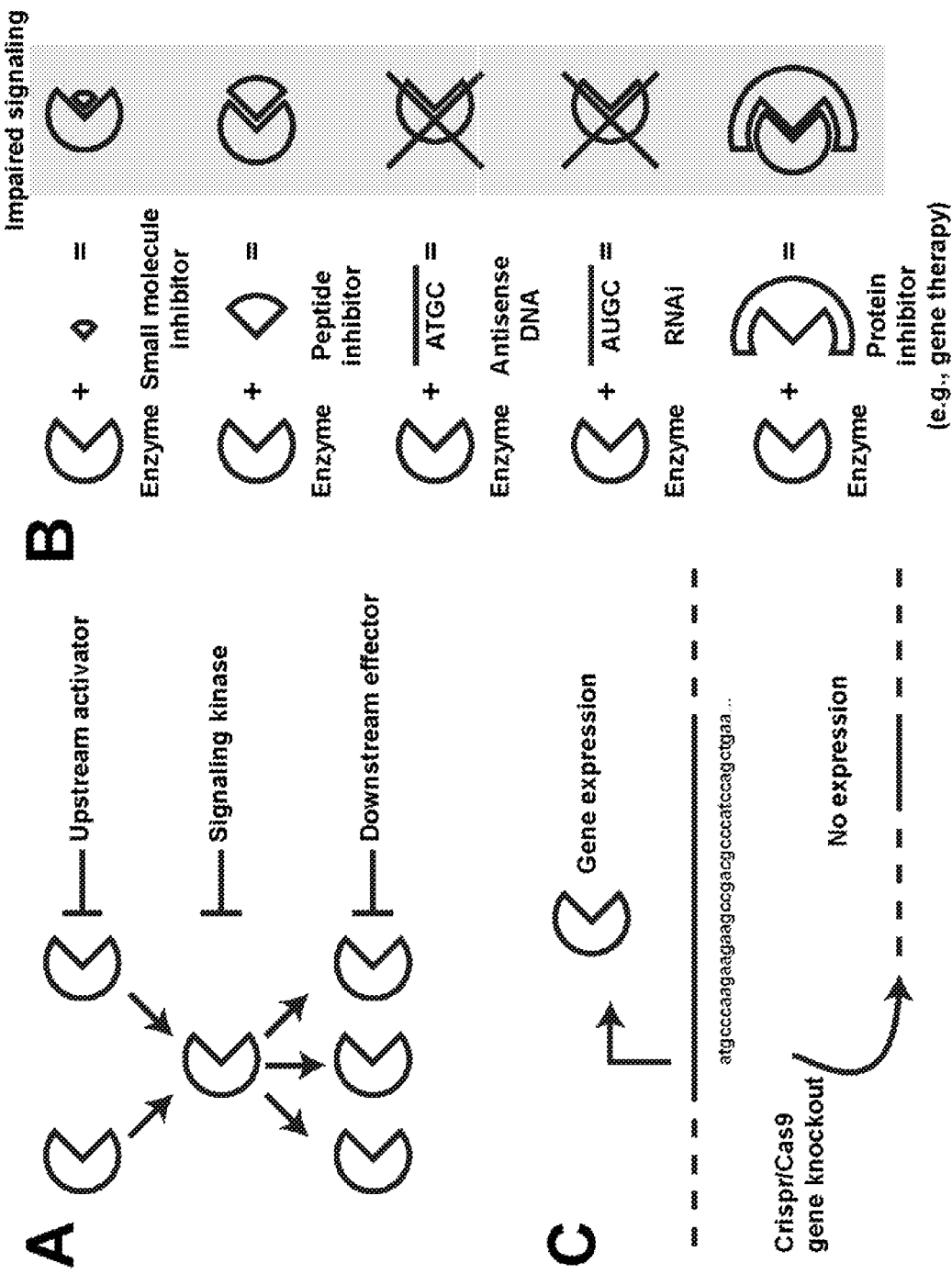
Figure 9:
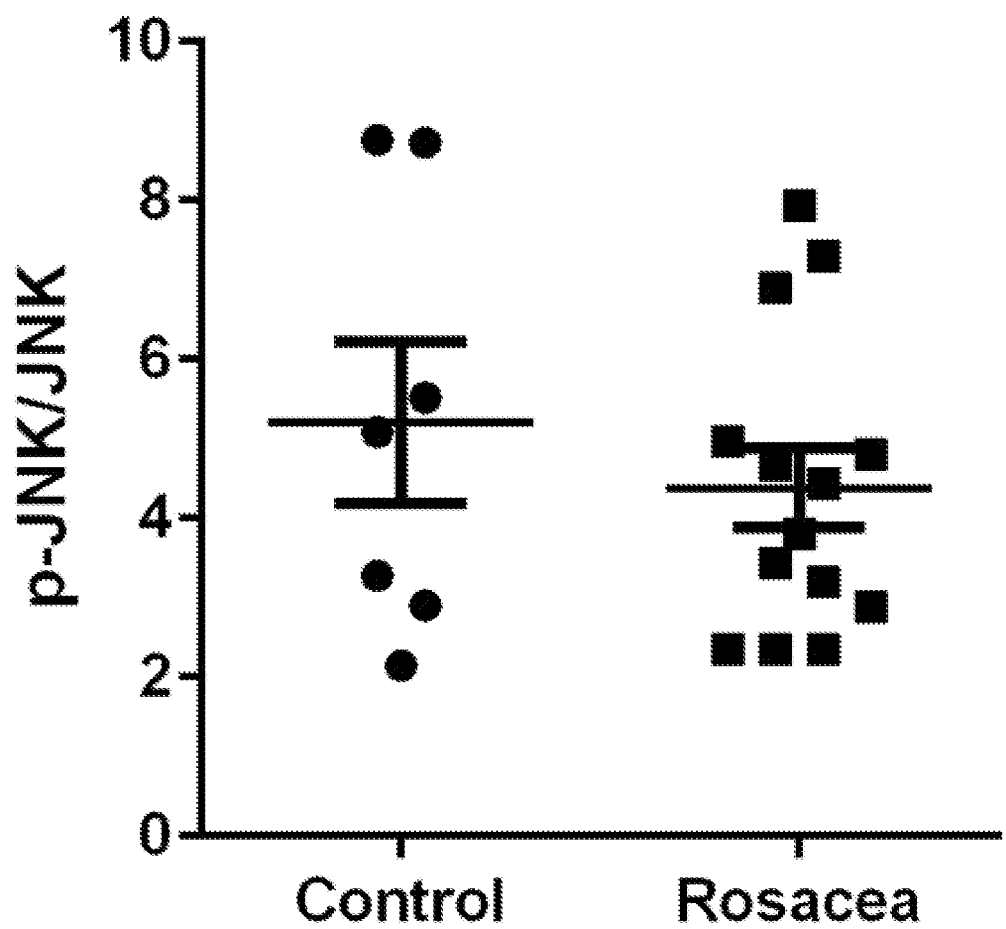

FIG. 6 is a series of images of the same mice as FIG. 5 immediately before or 7 hours after the application of the irritant solution where arrows mark the sites of application of the irritant solution; and FIG. 7 is a series of images of a histochemical analysis of the treated skin where arrows point to the accumulation of immune cells below the epidermis in the spots treated with the irritant solution and pretreated with vehicle cream, denoting an inflammatory response to the irritant solution and the accumulation did not occur in the spots treated with the irritant solution and pretreated with a cream containing trametinib;

FIG. 8 is a schematic of different strategies for implementing the present invention; and FIG. 9 is a graph showing the unpredictability of the relationship between kinase pathway involvement in rosacea.

DETAILED DESCRIPTION OF THE INVENTION

Referring to the figures, wherein like numerals refer to like parts throughout, the present invention involves the treatment of ocular rosacea with p38 and Erk kinase pathway inhibitors to prevent or minimize the skin reaction and thus totally or partially alleviate the rosacea manifestation. The present invention was premised on a careful analysis of the alteration of cell-signaling pathways that facilitate the development of rosacea, which led to the identification of discrete targets for highly specific therapeutic intervention in the management of rosacea. More specifically, the present invention involves the treatment of ocular rosacea with p38 and Erk kinase pathways inhibitors which are believed to block the initial reaction to rosacea triggers, and thus may make it possible to prevent or minimize the skin reaction, including treatment after a flare or when constant redness is present to reduce the irritation. By preventing or minimizing the skin reaction, it may be possible to totally or partially alleviate the rosacea manifestation. The findings detailed in this application show that a normal cellular component of the skin of the eyelid, the keratinocyte (KC), exhibits increased activation of two specific pathways, called the Erk and p38 pathways, even in the absence of a subjacent inflammatory condition. This discovery consists of a novel finding for one in the art and provides the rationale to support the claim that inhibition of these pathways may be used to treat ocular and other types of rosacea including treatment after a flare or when constant redness is present to reduce the irritation.

Example 1

Methods

Biopsies and Protein Extraction

Cutaneous biopsies resulting from lower lid ectropion surgery were taken and analyzed. The protocol was reviewed and approved by the Albany Medical College Institutional Review Board, and adhered to the tenets of the Declaration of Helsinki. Immediately after resection of skin from patients with rosacea and from age- and gender-matched controls, the specimens were frozen at −80 C for later retrieval. A total of 34 samples were obtained, although three patients were excluded from the analysis due to lower lid malposition leading to excessive irritation.

Each sample was thawed, weighed, and processed for protein extraction. For that, 300 μl ice-cold lysis buffer containing 1% Triton X-100 (Sigma-Aldrich) in PBS containing protease and phosphatase inhibitor cocktails (Roche) and 50 mM pervanadate (Sigma-Aldrich) was added to the sample together with 250 mg of zirconia/silica beads (Biospec Products Int). Then samples were homogenized through three cycles of 1 minute each on a Mini-Beadbeater-96 (Biospec Products Int). Samples were centrifuged at >12,000 g for 2 minutes at 4° C. and the supernatant was cleared by a second centrifugation for 15 minutes at >12,000 g for 2 minutes at 4° C. Lysates were aliquoted. Some aliquots received 1× volume of 2× Laemmli buffer and were boiled for 5 minutes. Then, samples were immediately stored at −80° C. until use.

Protein Arrays and Western Blot

Detection of 46 phosphoproteins was performed on Proteome Profiler™ Human Phospho-Kinase Array Kit membranes (R&D Systems) according to manufacturer's instructions using 100 μg of total protein. Western blots were performed using 10 μg/lane of total protein and detected using the following antibodies: pT180Y182 p38 (Cell Signaling 4511), pT202Y204 Erk1 (Santa Cruz Biotechnology sc-7383), total p38 (Santa Cruz Biotechnology sc-535), total Erk1/2 (Cell Signaling 9102) and Actin (Sigma-Aldrich A5441). HRP-conjugated secondary antibodies were from Jackson ImmunoResearch. Signal was detected with West Pico or West Femto reagents (Pierce) and a FujiFilm LAS-3000 imager. Band quantification was performed using FujiFilm MultiGauge software from raw image files according to manufacturer's instructions.

Immunohistochemistry

Paraffin sections were deparaffinized and rehydrated with sequential steps in xylene and ethanol solutions (100→95>70%). Endogenous peroxidase activity was blocked with 0.5% $H_2O_2$/MeOH for 10 minutes at room temperature (RT) and antigen retrieval was done 30 min at 100° C. in 10 mM citrate buffer, pH 6. Samples were blocked with 5% normal goat serum (Vector S-1000) for 1 hour at RT. Primary antibodies were incubated at a dilution 1:80 in PBS overnight at 4° C. Biotinilated anti mouse secondary antibody (Vector ba-9200) 1:500 in PBS were incubated for 1 hour at RT. Then, samples were incubated with avidin/biotin peroxidase (Vector ABC kit Elite PK-6100) in the dark for 30 min at RT and signal was detected with 3,3'-diaminobenzidine (Immpact DAB, Vector SK-4105) and counterstained with hematoxylin (Vector H-3404) prior to dehydration and mounting with Vecta-Mount (Vector H-5000). Positive cells were quantified per 1000× field.

Statistical Analysis

Ocular rosacea vs control samples were compared by Student's T test. A $p<0.05$ was considered statistically significant.

Results

In order to identify the mechanisms underlying ocular rosacea, the level of activation of multiple signaling pathways in diseased and control skin tissue was compared. A total of 34 samples were obtained, although three patients were excluded from the analysis due to lower lid malposition leading to excessive irritation.

The initial pathway characterization was performed in 8 samples using an unbiased approach consisting in the simultaneous analysis of 46 proteins. Lysates were allowed to bind to Proteome Profiler™ Human Phospho-Kinase Array Kit membranes (R&D Systems). Results are summarized in Table I below.

TABLE 1

| Phosphoprotein | Control (AU) | Rosacea (AU) | p value |
|---|---|---|---|
| p38 alpha (T180/Y182) | 214.6128 | 767.6414 | 0.004048 |
| ERK1/2 (T202/Y204, T185/Y187) | 301.6816 | 961.7494 | 0.091031 |
| JNK 1/2/3 (T183/Y185, T221/Y223) | 508.5686 | 334.213 | 0.335009 |
| GSK-3 alpha/beta (S21/S9) | 816.7295 | 396.0909 | 0.172968 |
| EGF R (Y1068) | 539.6214 | 275.2359 | 0.269187 |
| MSK1/2 (S376/S360) | 541.086 | 457.1573 | 0.552135 |
| AMPK alpha1 (T183) | 333.114 | 261.343 | 0.617421 |
| Akt 1/2/3 (S473) | 231.4213 | 284.4941 | 0.695334 |
| TOR (S2448) | 190.1555 | 594.5279 | 0.042689 |
| CREB (S133) | 240.4558 | 399.0289 | 0.001656 |
| HSP27 (S78/S82) | 532.9816 | 969.6496 | 0.174132 |
| AMPK alpha2 (T172) | 394.3459 | 717.9143 | 0.163357 |
| beta-Catenin | 292.4131 | 292.8966 | 0.997046 |
| Src (Y419) | 339.7041 | 302.9746 | 0.805285 |
| Lyn (Y397) | 398.7986 | 289.2499 | 0.304199 |
| Lck (Y394) | 385.5884 | 213.7605 | 0.125884 |
| STAT2 (Y689) | 879.1555 | 1417.081 | 0.105447 |
| STAT5a (Y699) | 472.9613 | 790.4458 | 0.040134 |
| Fyn (Y420) | 212.7338 | 391.9093 | 0.033901 |
| Yes (Y426) | 238.8639 | 339.5305 | 0.022155 |
| Fgr (Y412) | 198.5089 | 145.5631 | 0.133263 |
| STAT6 (Y641) | 364.3103 | 915.7491 | 0.028046 |
| STAT5b (Y699) | 321.626 | 701.1226 | 0.006747 |
| Hck (Y411) | 254.5958 | 453.9424 | 0.054826 |
| Chk-2 (T68) | 281.8076 | 357.9696 | 0.209134 |
| FAK (Y397) | 292.364 | 286.1925 | 0.9115 |
| PDGF R beta (Y751) | 262.0724 | 222.9519 | 0.522738 |
| STAT5a/b (Y699) | 301.6294 | 397.8481 | 0.283671 |
| PRAS40 (T246) | 735.7211 | 465.6334 | 0.315541 |
| p53 (S392) | 2171.036 | 2851.344 | 0.192892 |
| Akt 1/2/3 (T308) | 3989.069 | 4505.205 | 0.202167 |
| p53 (S46) | 3360.122 | 3813.075 | 0.089048 |
| p70 S6 Kinase (T389) | 728.0834 | 731.2244 | 0.979898 |
| p53 (S15) | 3581.397 | 3663.909 | 0.876948 |
| c-Jun (S63) | 3546.526 | 4461.907 | 0.100241 |
| p70 S6 Kinase (T421/S424) | 4266.741 | 4476.675 | 0.669157 |
| RSK1/2/3 (S380) | 5900.862 | 11343.56 | 0.040403 |
| eNOS (S1177) | 3175.718 | 3793.325 | 0.211349 |
| STAT3 (Y705) | 3331.626 | 4407.933 | 0.175331 |
| p27 (T198) | 923.5785 | 1238.758 | 0.079273 |
| PLC gamma-1 (Y783) | 2284.429 | 2417.716 | 0.584671 |
| STAT3 (S727) | 1733.881 | 2185.037 | 0.404835 |
| WNK-1 (T60) | 1845.118 | 2498.976 | 0.11562 |
| Pyk2 (Y402) | 2947.138 | 3233.06 | 0.614251 |
| HSP60 | 6713.87 | 12461.38 | 0.03298 |

Figure 1:
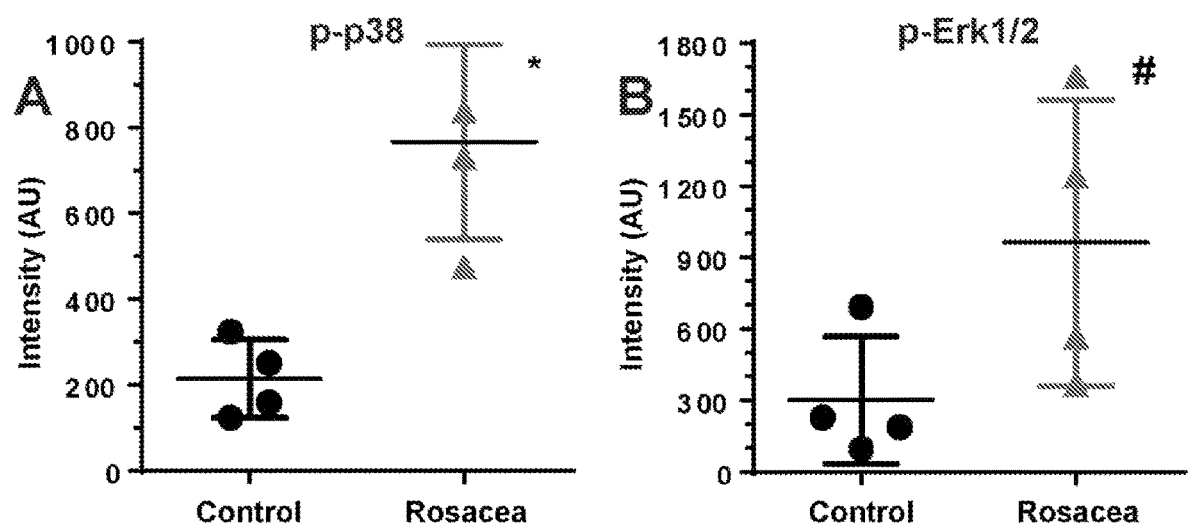

Among other signals, the levels of activation of p38 and Erk1/2 were increased in samples from patients with ocular rosacea when compared to samples from control patients without ocular rosacea (FIG. 1).

Figure 2:
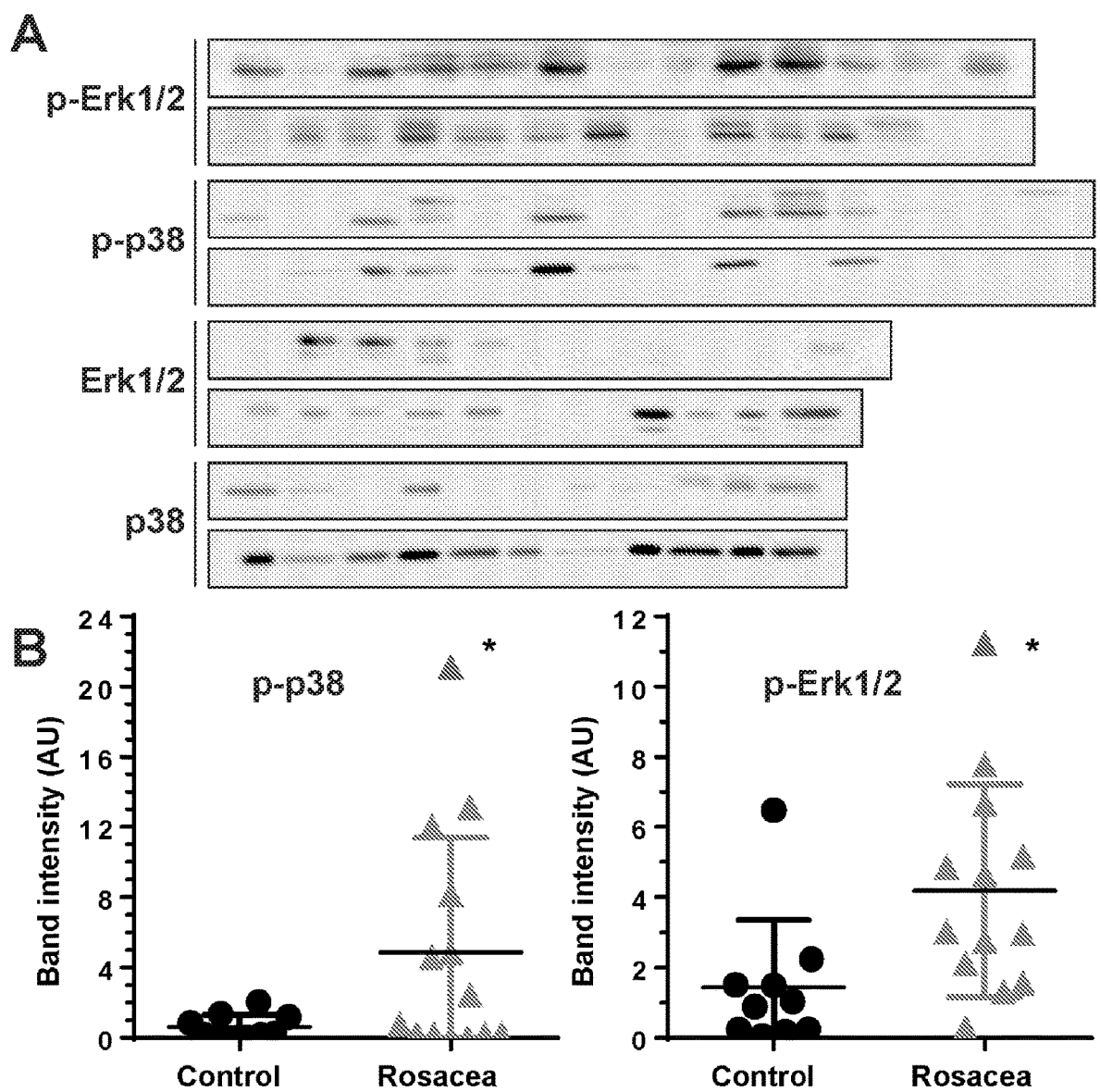

To confirm the results obtained by the phosphokinase array, the levels of pT180Y182-p38 (p-p38) and pT202Y204-Erk1 (p-Erk) were tested in the proteins extracted from these and other samples by Western blot analysis. FIG. 2A shows a sample of the band pattern obtained by the Western blots, while FIG. 2B shows the quantification of the data. Confirming the results obtained previously, a significant increase was observed in the levels of p-p38 and p-Erk1/2 in rosacea samples. Other signals were significantly increased in the proteome profiler array (Tor, CREB, Stat5a, Fyn, Yes, Rsk1/2/3 and HSP60), but subsequent analyses by Western blot were unable to confirm those results (data not shown).

Figure 3:
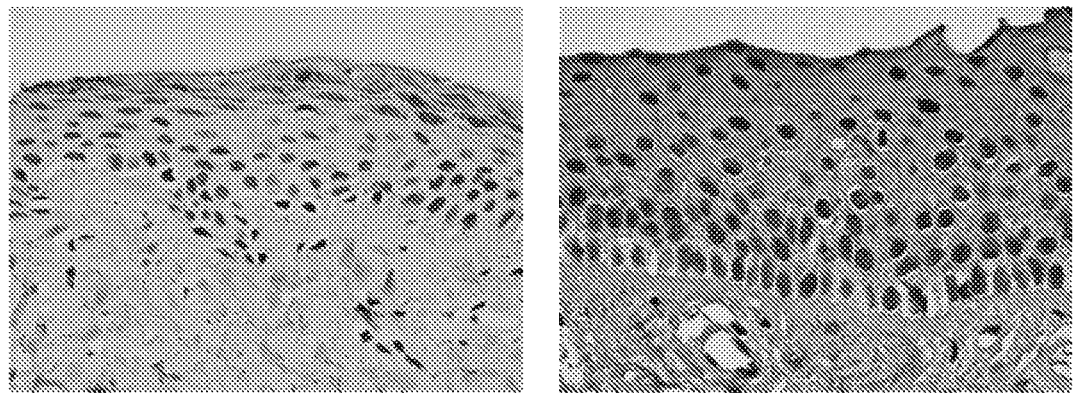
FIG. 3 is a graph of the immunohistochemical localization of p-p38 and p-Erk, where (A) are images of representative fields showing the marked epidermal localization of the phosphorylated proteins in the rosacea samples and (B) is the quantification of the number of positive cells/field. *, $p<0.05$ (Two-tailed Student's T test, n=12 controls and 12 rosacea eyelids)
Figure 3:
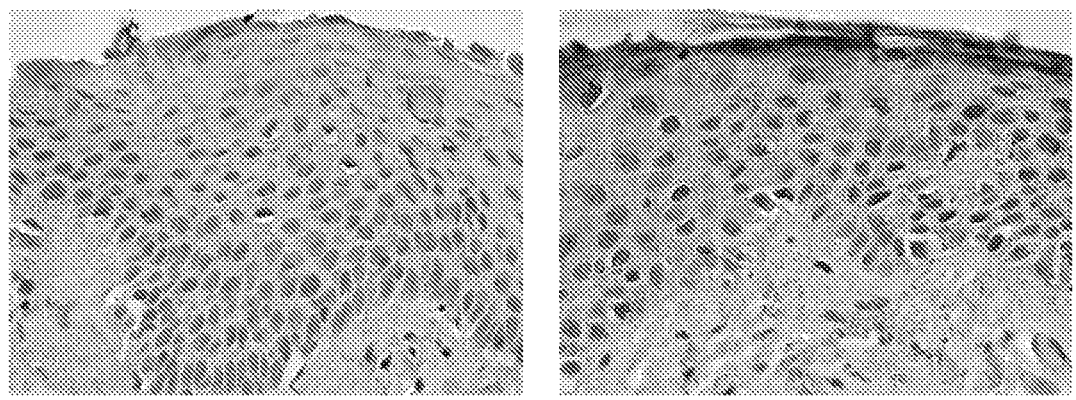
Figure 3:
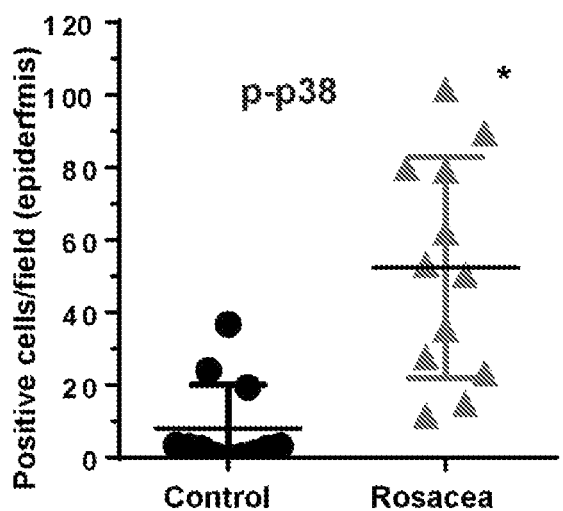
Figure 3:
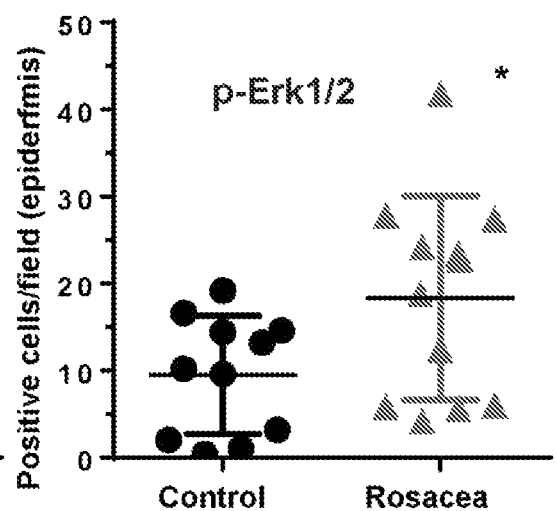

A determination of which cell type(s) within the skin displayed increased p-p38 and p-Erk1/2 levels was performed. Additionally, the enhanced concentrations of these candidate cell signals was confirmed, using a highly specific, low-throughput technique. Immunohistochemical analysis was performed on paraffin-embedded sections obtained from archived eyelid biopsies. As with previous assays, lower eyelid ectropion biopsies from patients with or without ocular rosacea were compared. As shown in FIG. 3A, the signal for these two activated protein species was almost exclusively located within the epidermis, suggesting that the keratinocyte is the main cell type responsible for the observed differences. Consistent with the overall increase of phosphorylated p38 and Erk observed in the protein array and Western blot assays, the numbers of epithelial cells that stained positively for these cell signals were statistically significantly higher in cutaneous biopsies of ocular rosacea than in age- and gender-matched controls (FIG. 3B).

DISCUSSION

The present invention is the first to implicate MAPK activation in the pathogenesis of this disorder and use that knowledge for treatment. Specifically, based on analyses that employed multiple different mechanisms to assess the enrichment of a wide array of individual kinases, activation of p38 and ERK were clearly increased in the epidermis of eyelids with ocular rosacea. This finding is highly unlikely to derive from non-specific interactions, as it was consistently observed using three different methodologies: chemiluminescent membrane-based antibody array and Western blot of Triton X-100 lysates, as well as immunohistochemistry of paraffin-embedded tissue sections.

Due to the lack of available animal models of rosacea, it is very difficult to test a causal relationship for any intracellular signal in preclinical studies. However, the findings of the present invention are consistent with the existing literature regarding cutaneous inflammation. Previous investigations have implicated toll-like receptors (TLR) in the pathogenesis of rosacea. These receptors can promote p38 and Erk activation in the context of other diseases and these pathways have been shown to mediate multiple keratinocyte responses. For example, TLR2-mediated p38 and Erk activation was required for the inflammatory and antimicrobial responses of keratinocytes challenged with streptococcal M1 protein, *Staphylococcus epidermidis* LP01 lipopeptide, or *Candida albicans* phospholipomannan. Moreover, the TLR4/p38 signaling axis is essential for normal cutaneous wound healing, and expression of TLR2 and TLR4 was found to be altered in other skin diseases such as atopic dermatitis, contact dermatitis and psoriasis. The identification of the increased activation of p38 and Erk signaling in diseased skin strongly suggest an active TLR/p38 axis as an important mechanism of ocular rosacea. This activation may ultimately yield increased cytokine levels, with then may result in some of the clinical manifestations of rosacea. Alternatively, Erk and p38 may signal independently of TLR.

Selective inhibition of p38 and ERK pathways thus represents an intriguing possibility for the management of rosacea. The absence of targeted remedies for this disease strongly indicates that cellular therapies would be a welcome addition to our interventional armamentarium. In fact, multiple active clinical trials are currently active to test safety and efficacy of p38 inhibitors in Langerhans cell histiocytosis as well as multiple inflammatory diseases, including chronic obstructive pulmonary disease, cardiovascular disease, and rheumatoid arthritis. Targeting MAPK signaling has thus been shown to have an acceptable safety profile. A large phase III trial to study the ability of Losmapimod (a selective p38 inhibitor) to reduce the incidence of cardiovascular events in subjects with acute coronary syndrome (LATITUDE-TIMI 60, NCT02145468) was recently finished. While the trial did not demonstrate efficacy, it demonstrated a good safety profile. Similarly, MEK1/2 (the upstream activator of Erk1/2) inhibitors are being currently tested in phase III trials for the treatment of multiple oncologic pathologies and Trametinib, a MEK1/2 inhibitor, has been approved for the treatment of melanoma containing BRAFV600E or V600K mutations. While other fields have adopted kinase inhibitors, the use of cellular therapies in the treatment of rosacea is a novel, highly exciting opportunity to enhance the lives of patients that suffer from this currently-incurable disease. By documenting a constitutive increase of p38 and ERK activation in this disease, the present invention indicates that agents that inhibit these cell signals in the treatment of rosacea may be effective including treatment after a flare or when constant redness is present to reduce the irritation.

Inhibitors which may be used in connection with the present invention include, without limitation, agents that can block or reduce p38 and Erk pathways. These agents may consist, without limitation, on small molecules, peptides and other biologics that can reduce the kinase activity of these kinases, their upstream activators or downstream substrates; agents such as RNA interference and antisense DNA that can reduce the expression of p38 or Erk kinases, their upstream activators or downstream substrates; gene therapy vectors such as naked DNA, liposome-enclosed DNA, adenovirus, adeno-associated virus, retrovirus or lentivirus encoding methods to block the expression of pathway activators, or to increase the expression of pathway inhibitors; gene therapy vectors to perform gene editing such as TALENs or Crispr/Cas9 methods or any other similar technology to modulate the activity of the p38 and/or Erk pathways.

Upstream activators include, without limitation, Rac1, Rac2, Rac3, CDC42, Ras family of proteins, Raf family of proteins, Mek1, Mek2, MKK3, MKK6, Ask1, Ask2, MEKK1, MEKK4 MLK1, MLK2, MLK3, Sos, Src, FAK, IRS1, IRS2 and IRS3 and any other molecule found to activate or inhibit a p38 or Erk kinases.

Downstream effectors include, without limitation, MSK1, MSK2, PRAK, p90RSK, Elk1, Creb, Myc, ATF2, ATF3, ATF4, MEF2, STAT1, STAT3, p53, MAPKAP2, HSP27, NFAT2, NFAT4, SRF, cPLA2, STMN1, Tau, Cdc25B, Max, GADD153 and Sap1 and any other molecule found to mediate the effects of p38 and Erk kinases.

Example 2

Wild type Balb/c mice of 6-8 weeks of age were used to determine the safety and efficacy of application of a cream containing an inhibitor of the Erk pathway. Animal studies were approved by the Albany Medical Center Institutional Review Board. The fur of the back was removed with an application of Nair. Three days later, three marks were made on the backs of the mice and treated with a cream containing trametinib (an Erk pathway inhibitor), vehicle cream (without an active ingredient) or nothing daily for five days. One hour after the last application, the spots were treated with one cream or the other, and cutaneous inflammation was induced via exposure to 1-Fluoro-2,4-dinitrobenzene (hereafter DNFB). Six hours later mice were euthanized and the skin spots were processed for histological analysis.

Figure 4:
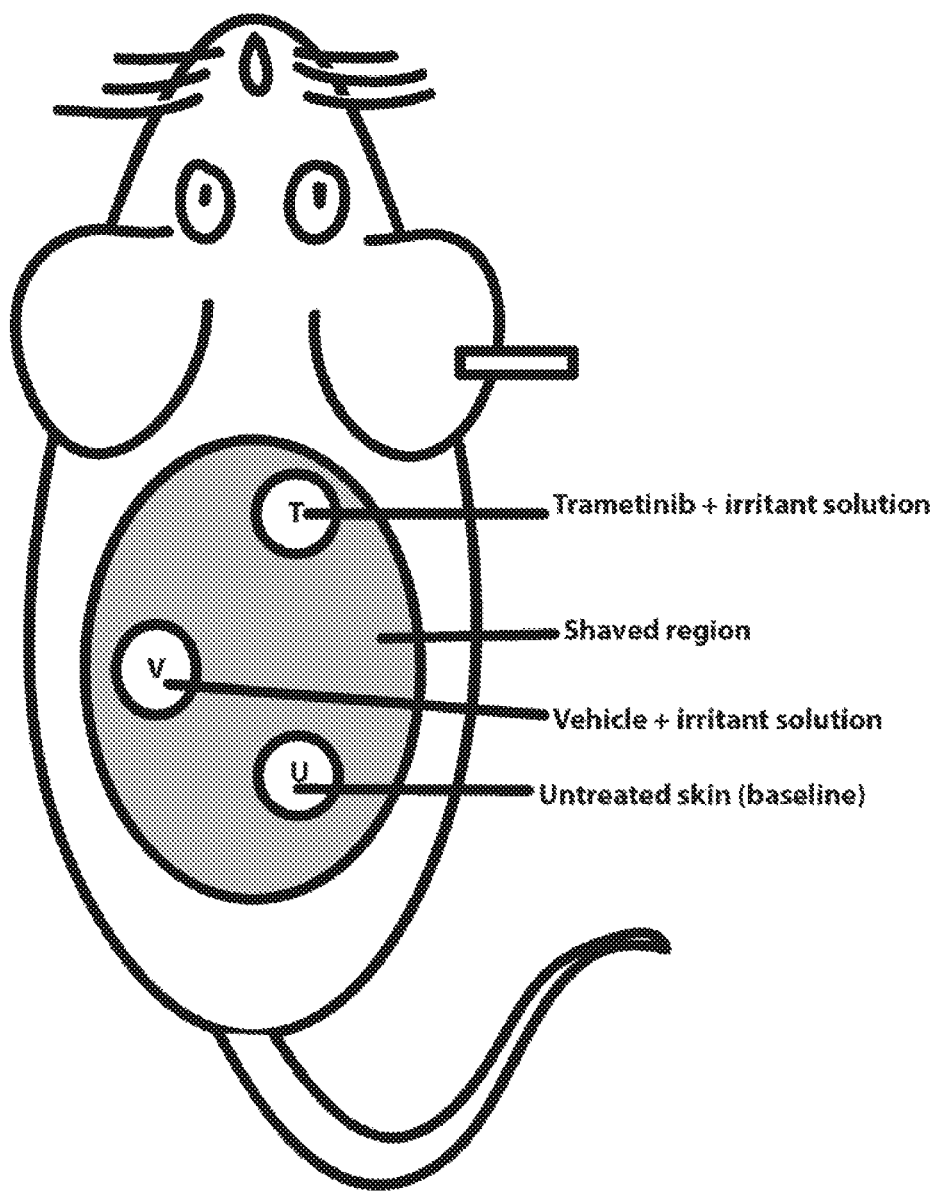
FIG. 4 is a diagram of the treatment protocol for Example 2 and identifying the labels V, T and U.

More specifically, to determine whether a cream containing an inhibitor of the Erk activation pathway would effectively penetrate the skin and protect it from an external injury, four mice were treated once a day for five consecutive days on a shaved back with a cream containing 0.1 mg/ml trametinib and cream without drug as described in FIG. 4. Regions labeled 'U' were left untreated and represent the baseline normal skin. Regions labeled 'V' were treated daily with a cream that does not contain an active ingredient (vehicle cream). Regions labeled 'T' were treated with a cream containing trametinib as the active ingredient. After five days, regions V and T were exposed to the irritant solution for 7 hours.

Photographs were taken daily and shown as FIG. 5. No skin changes can be observed after the application of either a vehicle cream or a cream containing trametinib, demonstrating no adverse effect of these creams in the period tested. At the fifth day, one hour after the last dose, the mice were exposed to a known skin irritant, 1-Fluoro-2,4-dinitrobenzene (hereinafter DNFB) dissolved in a mixture of 4 parts acetone and 1 part peanut oil to a final concentration of 0.5%. This mixture of DNFB, acetone and peanut oil is called hereinafter "irritant solution". A total of ten microliters of the irritant solution was applied to the back of each mouse in two positions as described in FIG. 6. Seven hours later, mice were euthanized and the treated skin spots were fixed in 4% PFA, embedded in paraffin and processed for histological analysis. Photographs of the backs were obtained prior to euthanasia. Images immediately before the application of the irritant solution and after 7 hours are shown in FIG. 6. It is clearly observed the irritation caused by the irritant solution on the spots treated daily with vehicle cream (labeled V in FIG. 6) as a red skin mark. This irritation is absent on the spots treated daily with a cream containing trametinib. The arrows mark the sites treated with the irritant solution.

Histological analysis of the skins after euthanasia confirmed these observations. Hematoxylin/Eosin (H&E) staining, a standard histological technique to study tissue architecture, shows that the irritant solution caused an inflammatory response in vehicle-treated spots that is strongly reduced in the spots treated with a cream containing trametinib. FIG. 7 shows the accumulation of immune cells below the epidermis of vehicle-treated spots (arrows) and the absence of such accumulation in the spots treated with a cream containing trametinib.

This example demonstrates that the inhibition of this specific pathway is a feasible approach that can have important beneficial effects on the skin when applied as a topical treatment. It also shows that this treatment does not elicit an acute adverse effect in the skin.

The present invention thus reveals that multiple strategies can be devised to block, alter or increase biochemical changes in living cells in order to modify cellular behavior and treat disease, and a different discrete feature of cell biology may be selectively manipulated with several different modalities. Most importantly, a thorough understanding of the aberrancies involved in a particular disease will necessarily involve the knowledge of all the interconnected proteins associated with a particular cellular response, which anyone in the art would recognize as a "signaling pathway". Achieving an effective change in a particular pathway without altering other pathways that may be necessary for normal cellular behavior is an optimal goal, so as to achieve a therapeutic effect with less collateral damage. One in the art will recognize that no protein acts in isolation, and a specific approach to block a pathway may involve the inhibition of one or more of the proteins in that pathway. Thus, alteration of different proteins may be designed with a single goal in mind. For example, blockade of the Erk pathway may be accomplished through the inhibition of Erk itself, its immediately upstream activators MKK1/2 or activators further upstream, such as Raf and Ras. Targeting any of these proteins will have the ultimate effect of inhibiting the effects of Erk and thus achieve the desired goal of the present invention.

One of skill in the art may also devise several strategies involving pharmacological agents with distinct structural features but that will necessarily share a common target protein within the cell. In particular, agents that inhibit a particular kinase may range from a small molecule compound or peptides that can prevent their kinase activity, activation, or binding to downstream targets, to large RNA and DNA molecules aimed at reducing or minimizing the total cellular content of such protein or the increase in contents of a second protein that has the ability to block the activity, activation, or binding to a downstream target of the target kinase, as seen in FIG. 8. In doing so, each strategy will achieve the same goal. One of skill in the art will appreciate that each strategy will have different advantages and disadvantages in terms of cost and facility of development, as well as specificity, effectiveness, period of activity, ability to reach a specific tissue and stability, among others. A choice of one specific pharmacologic strategy will thus depend on the evaluation of all these factors, as well as the continuous improvement of current strategies. Importantly, each strategy is not exclusive and two or more alterations can be combined to increase efficacy, either targeting the same protein or two different proteins within a pathway or in two different pathways. Referring to FIG. 8, A, blockade of a signaling pathway may be achieved by targeting different proteins involved in a particular pathway. For example, inhibition of Erk effects may be achieved through inhibition of Erk itself, its upstream activators MEK1/2 or by blocking effectors downstream such as Elk1 or Creb. B, different strategies designed to block the activity of proteins in the Erk and p38 pathways. These strategies will be implemented alone or in combination to achieve maximal inhibition with minimal side effects. Such strategies include the use of small organic compounds, DNA- or RNA-based gene knockdown, or expression of pathway inhibitors. C, an example of the strategy design using Crispr/Cas9- or Talen-based methods to remove a gene coding for a protein critical in the Erk or p38 pathways. Shown is a Crispr/Cas9-based method to remove the transcription start site of MEK1 to completely prevent MEK1 expression in the skin.

The inhibition of the Erk or p38 pathways may be accomplished by various methods. For example, organic compounds, usually ranging from 300 Da to less than 2000 Da have been found to prevent enzymatic activities with varying degrees of efficacy and selectivity. Examples of MEK kinase inhibitors include molecules that are competitive or non-competitive inhibitors of the ATP binding domain, allosteric inhibitors, as well as kinase domain inhibitors. Antisense DNA or RNAi approaches can be used to reduce the levels of kinase, thus achieving a reduction in its activity ("gene knockdown"). Examples of this approach include modified or non-modified nucleic acid sequences that are complementary to the MEK mRNA sequence. An example of such an approach would target MEK1 with the sequence TTTGTTCAGGAATTCTTCCAG (SEQ ID NO: 1) or any other suitable sequence. The oligonucleotide sequence can be delivered by itself, such as in siRNA approaches, or within a larger nucleotide sequence, such as in shRNA approaches. Delivery of these oligonucleotides can be achieved by several approaches. Most commonly, these nucleotides will be delivered in an aqueous solution ("naked" DNA or RNA), within charged lipids, within liposomes, or via viral vectors such as adenovirus, adeno-associated virus, lentivirus or retrovirus. A third approach includes the ability to selectively express an inhibitor of a pathway. As an example of such strategy, skin tissue would be engineered to express a phosphatase such as MKP1 that would remove the activating phosphate groups in Erk1/2 and thus turn it into its inactive state. In such a strategy, the upstream activating changes would be counteracted by the exogenous inhibitor. Common strategies to achieve exogenous expression of a protein include the transfection of tissues with plasmid polynucleotides that contain the full sequence coding for such inhibitor, as well as all other sequences required for gene expression, including but not limited to a promoter sequence, ribosomal binding sequences, polyadenilation sequences, etc. As with the gene knockdown approaches, delivery of this polynucleotide sequence can be achieved through naked DNA approaches, within charged lipids, within liposomes, or via viral vectors such as adenovirus, adeno-associated virus, lentivirus or retrovirus. A fourth approach takes advantage of newly-developed techniques to remove genetic information in tissues. Such an approach would include Talen, Crispr/Cas9 or other techniques to alter chromosomal DNA in the skin to eliminate a gene, either partially or completely, in order to block the protein expression. An example of this strategy may involve the removal of the transcription start site of MEK1 and MEK2 in the skin via viral delivery of Crispr/Cas9-based sequences.

Notably, work associated with the present invention revealed that different kinases have vastly different involvements with roasacea. Erk and p38 family of kinases share a similar protein structure. Moreover, their upstream activators MKK1/2 and MKK3/6 also are structurally related. A third family of kinases, JNK, is also structurally related to Erk and p38 kinases and its activators MKK1/4/7 are structurally and functionally homologous to MKK1/2 and MKK3/6. JNK activation is a common feature of many disease states in which cellular stress and inflammation occur. Referring to FIG. 9, the JNK proteins, however, were not activated in patients with rosacea, clearly demonstrating a specific activation of the Erk and p38 pathways and not an indiscriminate activation of all pathways involved in an inflammatory response.

The present invention thus encompasses a method of using a first pharmacological agent to selectively prevent the effects of the activation of the Erk pathway, including Erk, one of its upstream signaling activators, or one of its downstream effectors in the initiation, as a mechanism to prevent, alleviate or cure rosacea symptoms and underlying causes. The agent may be a small molecule compound. The first agent may be a synthetic peptide. The first agent may be a nucleic acid, such as antisense RNA or DNA to reduce the expression of pathway activators. The first agent may be a gene delivery system, such as naked plasmid DNA, liposome-enclosed DNA, adenovirus, adeno-associated virus, retrovirus or lentivirus encoding methods to block the expression of pathway activators, or to increase the expression of pathway inhibitors. The first agent may be a gene therapy vector to perform gene editing such as TALENs or Crispr/Cas9. The present invention also encompasses a method of using a second pharmacological agent to selectively prevent the effects of the activation of the p38 pathway, one of its upstream signaling activators, or one of its downstream effectors in the initiation, as a mechanism to prevent, alleviate or cure rosacea symptoms and underlying causes. The second agent may be a small molecule compound. The second agent may be a synthetic peptide. The second agent may be a nucleic acid, such as antisense RNA or DNA to reduce the expression of pathway activators. The second agent may be a gene delivery system, such as naked plasmid DNA, liposome-enclosed DNA, adenovirus, adeno-associated virus, retrovirus or lentivirus encoding methods to block the expression of pathway activators, or to increase the expression of pathway inhibitors. The second agent may be a gene therapy vector to perform gene editing such as TALENs or Crispr/Cas9. The method may also prevent concurrently the effects of the activation of p38 and Erk pathways as a mechanism to prevent, alleviate or cure rosacea symptoms and underlying causes. The upstream activators may include, without limitation, Rac1, Rac2, Rac3, CDC42, Ras family of proteins, Raf family of proteins, Mek1, Mek2, MKK3, MKK6, Ask1, Ask2, MEKK1, MEKK4 MLK1, MLK2, MLK3, Sos, Src, FAK, IRS1, IRS2 and IRS3 and any other molecule found to activate or inhibit a p38 or Erk kinases. The downstream effectors include, without limitation, MSK1, MSK2, PRAK, p90RSK, Elk1, Creb, Myc, ATF2, ATF3, ATF4, MEF2, STAT1, STAT3, p53, MAPKAP2, HSP27, NFAT2, NFAT4, SRF, cPLA2, STMN1, Tau, Cdc25B, Max, GADD153 and Sap1 and any other molecule found to mediate the effects of p38 and Erk kinases. The pharmacological agents may be provided in the form of pills or liquids or other suitable form for oral administration, in the form creams, lotions, oils, foams or other suitable form for topical administration, or in an injectable form suitable for systemic administration. One agent may be provided in a one form as and the other agent may be provided in a different form. The agents may also be combined with other beneficial agents, including, without limitation, ultraviolet light blockers, moisturizers, antibiotics, preservatives, fragrances, artificial colors or flavorings.

Acceptable kinase inhibitors according to the present invention may include: APS-2-79, ARRY-300, AZD8330, BAY86-9766, BI-847325, Binimetinib (MEK162, ARRY-162, ARRY-438162) Cobimetinib (GDC-0973, RG7420), E6201, GDC-0623, MEK162, MSC1936369B, Myricetin, PD0325901, PD184352 (CI-1040), PD318088, PD98059, Pimasertib (AS-703026), Refametinib (RDEA119, Bay 86-9766), Selumetinib (AZD6244), SHR7390, SL-327, TAK-733, Trametinib (GSK1120212), U0126, and WX-554 for MEK1/2; DEL-22379, FR 180204, GDC-0994, Pluripotin (SC1), SCH772984, Ulixertinib (BVD-523, VRT752271), and VX-11e for Erk1/2; AZ 628, BAY73-4506, CCT196969, CEP-32496, Dabrafenib, Encorafenib (LGX818), GDC-0879, GW5074, LY3009120, MLN2480, NVP-BHG712, PLX-4720, PLX7904, RAF265, R05126766, SB590885, Sorafenib, Sorafenib Tosylate, TAK-632, Vemurafenib (PLX4032, RG7204), and ZM 336372 for Raf; ARRY-371797/ARRY-797, AZD7624, AZD4547, BMS-582949, Doramapimod (BIRB 796), Glycyrrhizin, Losmapimod (GW856553X), LY2228820, Pamapimod (R-1503, Ro4402257), Pexmetinib (ARRY-614), PH-797804, SB202190 (FHPI), SB203580, SB239063, SB681323, SCIO-469, Skepinone-L, TAK-715, Tanzisertib(CC-930), VX-702, and VX-745 for p38; NQDI-1 and Selonsertib (GS-4997) for Ask1; AT13148, BI-D1870, LJH685, L11308, LY2584702, LY2584702 Tosylate, and PF-4708671 for Rsk/S6K; 6H05, Kobe0065, K-Ras(G12C) inhibitor 12, K-Ras(G12C) inhibitor 6, K-Ras (G12C) inhibitor 9, Salirasib, and Zoledronic Acid for Ras. It should be recognized that these inhibitors may easily be screened using the protocol of the Examples herein for efficacy.

Acceptable upstream promotor and downstream effector inhibitors according to the present invention may include: NSC 23766, Azathioprine, BQU57, CCG-1423, EHop-016, EHT 1864, ML141, ZCL278 for Rac/CDC42/Rho, Pifithrin-α (PFTα), Pifithrin-μ, and RITA (NSC 652287) for p53; S3I-201, APTSTAT3-9R, Artesunate, BP-1-102, Cryptotanshinone, Fludarabine, HO-3867, Napabucasin, Niclosamide, Nifuroxazide, SH-4-54, SH5-07 (SH-5-07), STA-21, and Stattic for STAT. It should be recognized that these inhibitors may easily be screened using the protocol of the Examples herein for efficacy.

What is claimed is:

1. A method of treating rosacea, comprising the step of administering a pharmaceutically effective amount of trametinib to a subject having ocular rosacea.

2. The method of claim 1, wherein the step of administering a pharmaceutically effective amount of trametinib includes concurrently administering an Erk kinase pathway inhibitor.

3. The method of claim 1, wherein the step of administering a pharmaceutically effective amount of trametinib comprises administering the pharmaceutically effective amount of trametinib topically.

4. The method of claim 1, wherein the step of administering a pharmaceutically effective amount of trametinib comprises administering the pharmaceutically effective amount of trametinib orally.

5. The method of claim 1, wherein the step of administering a pharmaceutically effective amount of trametinib comprises administering the pharmaceutically effective amount of trametinib by injection.

6. The method of claim 1, further comprising the step of administering a pharmaceutically effective amount of at least one agent selected from the group consisting of an ultraviolet light blocker, a moisturizer, an antibiotic, a preservative, a fragrance, an artificial color, a flavor, and combinations thereof.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: MEK kinase inhibitor

<400> SEQUENCE: 1
tttgttcagg aattcttcca g      21